United States Patent [19]

Roseman

[11] 4,043,339
[45] Aug. 26, 1977

[54] METHOD OF AND VAGINAL INSERT FOR PROSTAGLANDIN ADMINISTRATION

[75] Inventor: Theodore J. Roseman, Portage, Mich.

[73] Assignee: The Upjohn Company, Kalamazoo, Mich.

[21] Appl. No.: 654,486

[22] Filed: Feb. 2, 1976

[51] Int. Cl.$^2$ .................... A61M 7/00; A61J 13/08; A61J 27/00; A61M 31/00

[52] U.S. Cl. .................... 128/260; 424/305; 424/19; 128/130

[58] Field of Search ............ 128/260, 130, 270, 272; 424/19, 20, 21, 305, 318, 269, 28, 14, 16

[56] References Cited

U.S. PATENT DOCUMENTS

| | | | |
|---|---|---|---|
| 3,545,439 | 12/1970 | Duncan | 128/260 |
| 3,639,561 | 1/1972 | Gordon | 424/28 |
| 3,828,777 | 8/1974 | Ness | 128/260 |
| 3,852,465 | 12/1974 | Kirton et al. | 424/305 |
| 3,883,513 | 5/1975 | Hess et al. | 424/269 |
| 3,967,618 | 7/1976 | Zaffaroni | 128/130 |

OTHER PUBLICATIONS

*Prostaglandins*, Supplement to vol. 12, 1976, J. C. Cornette, et al. "Measurement of (15S)-15-Methyl Prostaglandin $F_{2\alpha}$".

*Prostaglandins*, Supplement to vol. 12, 1976, N. H. Lauersen et al., "Hormone Release & Abortifacient Effectiveness . . . etc."

*Prostaglandins*, Supplement to vol. 12, 1972, C. H. Spilman, et al., "Evaluation of Vaginal Delivery Systems . . . etc."

*Primary Examiner*—Aldrich F. Medbery
*Attorney, Agent, or Firm*—Earl C. Spaeth

[57] ABSTRACT

Novel vaginal devices containing prostaglandins and intended for use in accomplishing abortion in women in the first and second trimester of pregnancy and in inducing labor in pregnant women at or near term.

73 Claims, No Drawings

METHOD OF AND VAGINAL INSERT FOR PROSTAGLANDIN ADMINISTRATION

DESCRIPTION OF THE INVENTION

This invention relates to novel drug delivery devices and to methods for using them. More specifically, this invention relates to vaginal devices adapted for insertion and placement in the female human vaginal cavity and subsequent removal therefrom, for the administration of an abortifacient or oxytocic prostaglandin to the epithelial tissues of said cavity with the intent of accomplishing an abortion in a human during the first or second trimester of pregnancy or the induction of labor in a pregnant human at or near term.

Prostaglandins are related in structure to the substance known as prostanoic acid which has the formula and atom numbering:

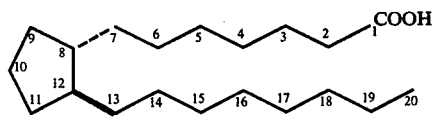
I

Numerous prostaglandins are known in the art. For example, the compound known as prostaglandin $E_2$ (PGE$_2$) has the formula:

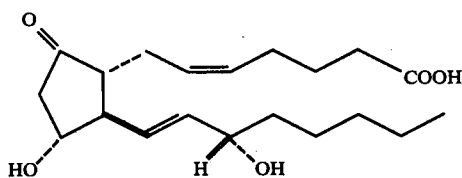
II and prostaglandin $F_{2\alpha}$(PGF$_{2\alpha}$) has the formula:

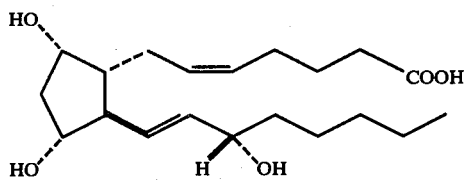
III

Other prostaglandins of the E-type and F-type are also known in the art. For example, PGE$_1$ lacks the 5,6-double bond of PGE$_2$, and PGE$_3$ has a cis-17,18-double bond but otherwise has the same structure as PGE$_2$. PGF$_{1\alpha}$ and PGF$_{3\alpha}$ differ from PGF$_{2\alpha}$ in the same manner. PGF$_{2\beta}$ has the same structure as PGF$_{2\alpha}$ except that 9-OH is attached in $\beta$-configuration. PGA-type prostaglandins all have the ring:

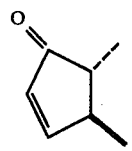
IV and PGB-type prostaglandins all have the ring:

V

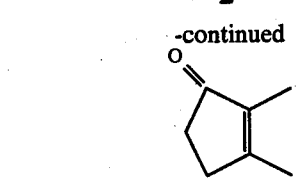

but otherwise these are the same in structure as the PGE-type and PGF-type prostaglandins. A very large number of other prostaglandins are also known in the art. These differ from the above-mentioned prostaglandins in one or more of various structural features. For example, one or more of the stereochemical features of the prostaglandin structure are altered, one or more of a large variety of substituents at one or more of the various positions on the prostaglandin structure are present, the length of either or both chains is different than in the prostaglandins, one of the oxygen atoms attached to the ring is absent, or any of a large variety of different structural features is introduced into one or both chains, for example, an oxa or a thia atom or a phenylene moiety in place of one or more of the methylene groups in a chain. One example of these is (15S)-15-methyl-PGF$_{2\alpha}$, having the formula

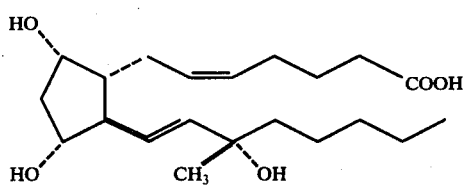
VI

The "15S" in this name refers to the stereochemical configuration of the attachment of the hydroxy to the side chain at C-15. It will be observed that this particular stereochemical feature is also present in the prostaglandins shown above in formulas II, and III. Prostaglandins with the opposite stereochemical configuration at C-15, known as 15R compounds, are also known in the art.

Some prostaglandins have been isolated from various mammalian tissues and fluids, for example, sheep vesicular glands and human seminal plasma. See, for example, Bergstrom et al., Pharm. Rev. 20, 1 (1968). For this reason, some publications make a distinction for classification purposes between the naturally occurring prostaglandins and their simple derivatives, for example, salts and esters, and the compounds which differ from those in one or more structural features, referring to the latter as prostaglandin analogs. For the purposes of defining and discussing the abortifacient and oxytocic compounds which are present in the novel vaginal devices of this invention, that distinction will not be made, and the terms abortifacient prostaglandin and oxytocic prostaglandin are to be construed as including all naturally occurring prostaglandins and their simple derivatives and all structural variations of those which approximate the basic structure of the natural prostaglandins and which cause prostaglandin-like abortifacient or oxytocic effects in pregnant female humans to a sufficient degree to be operative for the desired purposes.

It is known to use prostaglandins to accomplish abortions in female humans during the first and second trimesters and to induce labor in pregnant human females at or near term. See, for example, Ann. N.Y. Acad. Sci., 180, pp. 436–568 (1971); Karim, "The Prostaglandins", Medical and Technical Publishing Co., Ltd., Oxford, England, pp. 71-164 (1972); "The Prostaglandins, Clinical Applications in Human Reproduction", E. M. Southern, Editor, Futura Publishing Co., Inc., Mount Kisco, N.Y., pp. 77-239 and 295-545 (1972); "International Conference on Prostaglandins", Advances in the Biosciences 9, Pergamon Press, Elmsford, N.Y., pp. 507-598 (1973) and "The Prostaglandins", P. W. Ramwell, Editor, Plenum Press, New York, N.Y., Vol. 1, pp. 365-389 (1973). See also Béguin et al., Prostaglandins 1, 397 (1972); Toppozada et al., Prostaglandins 2, 239 (1972); Karim et al., J. Obst. Gyn. Brit. Cmw. 78, 294 (1971); ibid. 79, 737 (1972); Wiqvist et al., J. Reprod. Med. 9, 378 (1972); Karim et al., J. Reprod. Med. 9, 383 (1972); and Tredway et al., Am. J. Obstet. Gynecol. 116, 795 (1973). See also Bygdeman et al., Prostaglandins 8, 157 (1974); Corson et al., Prostaglandins, 9, 975 (1975); Leader et al., Prostaglandins 10, 357 (1975); Gutknecht et al., J. Reprod. Med. 15, 93 (1975); and Spilman et al., Contraception 11, 409 (1975). See also U.S. Pat. Nos. 3,778,506; 3,852,465; 3,882,241, and 3,899,587. See also references cited in each of the above. With particular regard to the use of (15S)-15-methyl-PGF$_{2\alpha}$ and its esters, see U.S. Pat. No. 3,728,382.

It is also known to use prostaglandins to evacuate the uterus of female humans when said uterus contains a dead fetus or a hydatidiform mole, or a combination of those. See, for example, Karim, "The Prostaglandins", above cited, especially pages 107-113 thereof. For the purposes of defining this invention, these uses of prostaglandins will be considered as abortions even though said dead fetus may in some instances be present after the end of the second trimester of pregnancy.

It is also known to use prostaglandins early during the first trimester of pregnancy including soon after an expected but missed menstrual period to induce menstruation in ovulating women who have had unprotected intercourse during mid-cycle. Thus, if a fertilized ovum or an early differentiation product thereof is present, it is removed. See, for example, Karim, "The Prostaglandins", above cited, especially pages 128-131 thereof. In defining this invention, this use of prostaglandins will be considered as abortion.

Various routes of administration of the prostaglandin for abortion or for labor induction have been suggested, including intravenous, intramuscular including myometrial muscle, subcutaneous, intra-amniotic, intravaginal, intra-uterine, and oral routes. Of these various routes, the vaginal route offers the substantial advantages of (a) being accessible for administration of the prostaglandin by paramedical persons, by nurses, or even by persons relatively untrained in medical techniques of drug administration, including the patient herself, (b) being in close tissue proximity to the target organ, namely the uterus, and, perhaps most important, (c) being the route of administration with the greatest potential for control of the administration of the prostaglandin with particular respect to stopping said administration should an undesirable response of the patient be observed. Once there has been an oral, intravenous, intramuscular, subcutaneous, intra-uterine or intra-amniotic injection of a substantial amount of the prostaglandin, the prostaglandin cannot be retrieved even though in some instances of unexpected and undesirable side effects, that might be desired. Therefore, multiple small doses or slow continuous dosage are indicated for maximum safety. But vaginal contents are easily evacuated, making possible easy and rapid removal of prostaglandin not yet absorbed by the epithelial tissues of the vaginal walls.

Various means and techniques for vaginal administration of prostaglandins for various purposes are known in the art. See, for example, U.S. Pat. Nos. 3,545,439; 3,625,214; 3,710,795; 3,896,819; and 3,920,805. See also, for example, Karim et al., J. Obst. Gyn. Brit. Cmw. 78, 294 (1971), above cited, and Béguin et al., Tredway et al., Bygdeman et al.; and Leader et al., all above cited. Various means and techniques for vaginal administration of other drugs are also known in the art. See, for example, U.S. Pat. Nos. 3,261,353; 3,312,215; 3,641,237; 3,797,494; and 3,892,238, and German Offenlegungsschrift 2,158,226. Various means and techniques for intrauterine administration of prostaglandins and other drugs are also known in the art. See, for example, U.S. Pat. Nos. 3,598,115; 3,699,951; 3,777,015; 3,887,699; 3,888,975; 3,892,842. Although intrauterine administration means and techniques usually involve entry into the human uterus through the external cervical os and thus initial entry into the vagina, the problems of drug delivery to the uterus are quite different than the problems of drug delivery to vaginal epithelial tissue. Therefore the means and techniques for drug delivery to the uterus are not relevant or applicable to vaginal administration of prostaglandins.

In spite of the relatively extensive body of prior art relating to vaginal administration of prostaglandins and other drugs as exemplified above, there still remains a need for better means and techniques for vaginal administration of abortifacient prostaglandins to accomplish an abortion in a human during the first or second trimester of pregnancy, and for administration of oxytocic prostaglandins to accomplish the induction of labor in a pregnant human at or near term. For example, there is a need for prostaglandin delivery systems which are easier and less expensive to manufacture than the prior art delivery systems, which are easily inserted into the vagina by persons with little or no medical training and experience, including the patient herself, which need be inserted only once to accomplish the desired abortion or induction of labor, which are retained in the vaginal cavity even during periods when the woman engages in mild physical activity, for example, sitting, standing, or walking as opposed to complete bed rest, which are easily removed when the abortion is accomplished or labor induced or when it becomes desirable for some medical reason, which are not wasteful of the relatively expensive prostaglandins in terms of the delivery system containing substantially more of the prostaglandin than is necesssary to accomplish the desired result, and perhaps most important, whose use will provide medically acceptable release rates of the prostaglandins to the vaginal epithelial tissues and whose design and construction will permit use of prostaglandins of varying degrees of abortifacient or oxytocic potency and varging degrees of lipophilicity. None of the prior art means, techniques, or delivery systems for vaginal administration of prostaglandins or of any other drugs satisfy all of these criteria.

I have now invented certain novel vaginal delivery systems which do satisfy the above criteria. One of these is a vaginal device adapted for insertion and placement in the female human vaginal cavity and subsequent removal therefrom, for the administration of an abortifacient or oxytocic prostaglandin to the epithelial tissues of said cavity, said device consisting essentially of a flexible resilient nontoxic polysiloxane elastomer substantially uniformly impregnated except at the elastomer surface with at least an effective amount of said abortifacient prostaglandin to accomplish an abortion in a human during the first or second trimester of pregnancy or with at least an effective amount of said oxytocic prostaglandin to accomplish the induction of labor in a pregnant human at or near term, said prostaglandin being present in free acid form or in a more lipophilic ester form, said device having two substantially parallel relatively large elastomer surfaces with combined surface area at least 70 percent of the total elastomer surface area of the device, both of said parallel surfaces being able to contact vaginal epithelial tissue, there being substantially no prostaglandin at said parallel elastomer surfaces of said device prior to vaginal insertion, the combination of the total elastomer surface area of said device and the concentration of prostaglandin in said device being suitable for a medially acceptable release rate of said prostaglandin in the human vagina to accomplish said abortion or said induction of labor, and the combination of the resilience of said elastomer and the distance between said parallel elastomer surfaces being such that both of said parallel elastomer surfaces remain either in contact with said epithelial tissues or exposed to the fluids in said vaginal cavity when said device is in the vaginal cavity.

Another of these novel vaginal delivery systems which I have invented and which satisfies the above criteria is a vaginal device adapted for insertion and placement in the female human vaginal cavity and subsequent removal therefrom, for the administration of an abortifacient or oxytocic prostaglandin to the epithelial tissues of said cavity, said device consisting essentially of a laminate having two substantially parallel relatively large surfaces with combined surface area of at least 70 percent of the total surface area of the device, both of said parallel surfaces being able to contact vaginal epithelial tissue, said device having a layer consisting essentially of a flexible resilient non-toxic polymeric solid substantially free of prostaglandin, with a shape and surfaces substantially the same as said device but with total linear dimensions smaller than those of said device, said solid bonded on one or both of its relatively large parallel surfaces or on all of its surfaces to a coextensive layer of a flexible resilient nontoxic polysiloxane elastomer substantially uniformly impregnated except at the outer elastomer surface with a total of at least an effective amount of said abortifacient prostaglandin to accomplish an abortion in a human during the first or second trimester of pregnancy or of at least an effective amount of said oxytocic prostaglandin to accomplish the induction of labor in a pregnant human at or near term, said prostaglandin being present in free acid form or in a more lipophilic ester form, there being substantially no prostaglandin at the outer elastomer surfaces prior to vaginal insertion, the combination of the total outer elastomer surface area of said device and the total concentration of prostaglandin in said elastomer being suitable for a medically acceptable release rate of said prostaglandin in the human vagina to accomplish said abortion or said induction of labor, the resilience of said device being such that the elastomer on one or both of said parallel surfaces of said device is either in contact with said epithelial tissues or exposed to the fluids in said vaginal cavity when said device is in said vaginal cavity.

Both of these two novel types of vaginal devices are used to accomplish an abortion in a female human during the first or second trimester of pregnancy by inserting either device into the vaginal cavity of said human. Also, both of these two novel types of vaginal devices are used to induce labor in a pregnant female human at or near term by inserting either device into the vaginal cavity of said human. Also, both of these two novel tyes of vaginal devices are used to induce menstruation in a sexually exposed female human after copulation, and capable of ovulating by inserting either device into the vaginal cavity of said human at a time after the time of expected but missed menses, preferably at a time at least two weeks after the time of expected but missed menses. Also, both of these two novel types of vaginal devices are used to empty the uterus of a human female when said uterus contains a dead fetus, a hydatidiform mole, or a combination of those, by inserting either device into the vaginal cavity of said human.

In the above description of these two novel types of devices, the term abortifacient prostaglandin is defined as that term is defined in U.S. Pat. No. 3,852,465, namely a prostaglandin which will cause an abortion when administered by one of the known routes of administration to a pregnant femal human or a pregnant female laboratory animal such as the rhesus monkey (Macaca mulatta). There is also described in said U.S. Pat. No. 3,852,465 a standard experimental mammal, the golden hamster, and a standard procedure for using those animals in determing easily whether a particular prostaglandin is an abortifacient prostaglandin. For the purposes of said U.S. Pat. No. 3,852,465, a prostaglandin is considered to be an abortifacient prostaglandin if it is abortifacient according to this golden hamster pregnancy test. That same definition of abortifacient prostaglandin is to be used in defining the present invention.

As disclosed in said U.S. Pat. No. 3,852,465, it is convenient to consider the effectiveness of the prostaglandin known as $PGE_2$ (formula II above) as standard in this testing procedure. With this standard in mind, the most useful vaginal devices of this invention for accomplishing abortions according to this invention, including induction of menstruation as described above and removal of a dead fetus or a hydatidiform mole or both from the uterus also as described above, will be those which contain an abortifacient prostglandin which is at least as effective, i.e., at least as potent, as $PGE_2$ in the golden hamster pregnancy test. Preferably the abortifacient prostaglandin is one which has a potency in the golden hamster pregnancy test at least 10 times that of $PGE_2$. Most preferred are the abortifacient prostaglandins which have potencies in the golden hamster pregnancy test at least 100 times that of $PGE_2$.

Examples of specific abortifacient prostaglandins useful for the purposes of said U.S. Pat. No. 3,852,465 are disclosed therein. Those prostaglandins are also useful for the purposes of the present invention within the limits set forth below.

Among abortifacient prostaglandins, preferred are those of the $PGF_\alpha$-type. See formula II and related discussion above. Especially preferred are prostaglandins of the $PGF_{2\alpha}$-type. More especially preferred are the free acid form and more lipophilic esters of (15S)-15-methyl-$PGF_{2\alpha}$. See formula IV above. With regard to that compound, preferred are the methyl and ethyl esters rather than the free acid form, especially the methyl ester.

The entire disclosure of said U.S. Pat. No. 3,852,465 is incorporated by reference herein.

The above descriptions of the novel vaginal devices of this invention also use the term oxytocic prostaglandin. Here, oxytocic is used in its customary medical sense as defining a substance which will induce labor in a pregnant woman at or near term. Accordingly an oxytocic prostaglandin is one which will induce labor in a pregnant woman at or near term. A useful laboratory animal for determining whether a particular prostaglandin is a oxytocic prostagladin is the rhesus monkey (*Macaca mulatta*). See, for example, Kirton et al., N.Y. Acad. Sci. 180, 445 (1971); Fuchs et al., ibid. 531; and Kirton et al., Prostaglandins 1, 319 (1972). All that need be done in this regard is to observe the response of the monkey uterus, measured as described in these articles, to prostaglandins administered as described in these articles at any time during monkey pregnancy after about 8 to 10 weeks of pregnancy. It is not necessary that the monkey be at term and labor actually induced by the prostaglandin. $PGE_2$ and $PGF_{2\alpha}$ are useful standards against which to measure other prostaglandins to determine their potential as oxytocic agents.

Also in the above descriptions of the two novel types of vaginal devices of this invention, it is specified that the abortifacient or oxytocic prostaglandin be present in free acid form or more lipophilic ester form. Most prostaglandins have a carboxyl group as a characteristic structural feature, although prostaglandins are known which have groupings of atoms in place of the carboxyl group which mimic the acidity of carboxylic acid. See, for example, U.S. Pat. No. 3,883,513. Such prostaglandins are included within the scope of this invention provided that they are suitably abortifacient or oxytocic.

An aqueous solution containing a prostaglandin in free acid form will usually contain some prostaglandin molecules in the anion form along with an amount of hydronium ions appropriate to the pH of the solution. The vaginal devices of this invention impregnated with the free acid form of the prostaglandin will thus deliver to the vaginal epithelial tissues or to aqueous vaginal fluids some prostaglandin molecules in anionic form. Such devices are not for that reason outside the scope of the novel vaginal devices of this invention. But vaginal devices in accord with this invention impregnated with a salt form of a prostaglandin, for example the THAM salt, are not within the scope of this invention unless other structural features of the prostaglandin are such as to give an overall lipophilicity to said salt form at least equal to the lipophilicity of the free acid form of $PGF_{2\alpha}$.

As mentioned above, an alternative to the free acid form of a prostaglandin in the novel vaginal devices of this invention are the more lipophilic ester forms. By this is meant various ester forms of a particlar prostaglandin which are more lipophilic than that particular prostaglandin in free acid form. Lipophilicity of a prostaglandin in free acid form or in ester form is easily measured by adding the prostaglandin to an equilibrated mixture of n-octanol and water, and shaking the mixture until the system is at equilibrium, preferably at about 25° C. The amount of prostaglandin in water layer and in the n-octanol layer is then measured by methods known in the art, the partition coefficient then being calculated as the concentration in amount of prostaglandin per unit volume of n-octanol layer divided by the amount of prostaglandin per unit volume of water layer. The larger the partition coefficient, the more lipophilic the prostaglandin. The amount of prostaglandin used in this test of lipophilicity should not, of course, exceed the amount which would equal the maximum solubility of the prostaglandin in the water layer of the system.

Among esters of abortifacient and oxytocic prostaglandins, preferred are the alkyl esters wherein the alkyl group contains one to 12 carbon atoms, inclusive. More preferred are alkyl esters wherein the alkyl group contains one to 4 carbon atoms, inclusive, especially the methyl and ethyl esters, more especially the methyl esters.

Vaginal devices according to this invention containing a prostaglandin ester which is some more lipophilic than the corresponding free acid of that prostaglandin usually have more desirable prostaglandin release rates in contact with vaginal epithelial tissues or the aqueous vaginal fluids than do devices which contain the free acid form. However, prostaglandin esters which are highly lipophilic may not be adequately absorbed by said tissues. Thus there is an upper limit to lipophilicity of the ester to be used. But this upper limit is defined by the abortifacient or oxytocic properties of the prostaglandin ester as measured by the golden hamster pregnancy test and the monkey oxytocic test described above.

Especially preferred among the novel vaginal devices of this invention for the abortifacient and oxytocic purposes of this invention are prostaglandins with lipophilicity at least as great as that of (15S)-15-methyl-$PGF_{2\alpha}$ in free acid form, most especially with lipophilicity about the same or greater than the methyl ester of that particular prostaglandin.

In the above descriptions of the novel vaginal devices of this invention, use of a flexible resilient non-toxic polysiloxane elastomer is specified as a matrix or vehicle to be impregnated with the abortifacient or oxytocic prostaglandin. Appropriate polysiloxane elastomers, methods for preparing them, and methods for impregnating them with prostaglandins and other drugs are well known in the art. See, for example, U.S. Pat. Nos. 3,545,439 and 3,920,805, and Kirk-Othmer, "Encyclopedia of Chemical Technology", Interscience Publishers, New York N.Y., 2d. Ed., Volume 18 pp. 221-260 (1969), and references cited in those. These polysiloxane elastomers are also known as silastic or silicone rubbers.

Typically, polysiloxane elastomers are prepared by polymerization of corresponding liquid polysiloxane prepolymers. Some such liquid prepolymers are converted to a rubber or elastic form by heat curing or vulcanization. Others, known as the RTV or room temperature vulcanication type, are transformed or vulcanized to the rubber or elastomer form in the presence of a catalyst, usually in the range about 20° to 40° C., the higher temperatures causing the polymerization (vulcanization) to occur at what is sometimes a more convenient rate of production purposes.

The prostaglandin-impregnated polysiloxane elastomer portions of the novel vaginal devices of this invention are intended to be of the solid suspension type prepared by encapsulating the prostaglandin in the polymeric elastomer environment. Typically, the prostaglandin is suspended in rather viscous but still liquid polysiloxane prepolymer by levigation. Then the mix is placed in molds of the desired geometry and polymerized.

It is intended when these novel vaginal devices are used according to this invention, that the prostaglandin which has dissolved in the final polysiloxane elastomer will migrate by diffusion to the surface of the device where it will then partition into the aqueous environment of the vagina. Encapsulted but undissolved prostaglandin will continue to dissolve to replace dissolved prostaglandin which has diffused from any particular part of the elastomeric matrix.

It is also intended that the release of prostaglandin from these novel vaginal devices be solely by this diffusion process. Therefoe it is important to choose polysiloxane prepolymers and vulcanization procedures such that the resulting polysiloxane elastomer is substantially homogenous like which would allow water permeation of the matrix and thus a leaching of drug from within the matrix. The choice of such polysiloxane prepolymers and procedures for vulcanizating them are within the skill of the art. Preferred are the dimethylpolysiloxane prepolymers of the RTV type, catalytically polymerizable in the range 20°–40° C. Various of the known tin-containing catlysts are suitable for this polymerization, for example, stannous octanoate or, more precisely stannous 2-ethylhexanoate.

Also as is known in the polysiloxane elastomer art, the presence of various fillers, especially finely divided silica, in the liquid polysiloxane prepolymer results in elastomers with physical properties especially with regard to tensile strength and resilience which are more suitable for the requirements of the novel vaginal devices of this invention. Here also, knowing those requirements as set forth herein, it is within the skill of the polysiloxane elastomer art to choose appropriate polysiloxane prepolymer-filler-mixtures for the production of said devices. The term polysiloxane elastomer as used herein is to be construed as including fillers when their presence is desired.

It is also necessary to chose polysiloxane elastomers and methods for producing them which will permit medically acceptable and medically appropriate release rates to accomplish the desired medical effects, i.e., abortion or iduction of labor. Whether a particular vaginal device will provide such a release rate will depend not only on the particular elastomer matrix but also on the geometry of the device. Methods for measuring in vitro and in vivo release rates of these vaginal devices are described below.

In the above descriptions of the novel vaginal devices of this invention, it is specified that the devices each have two substantially parallel relatively large elastomer surfaces with combined surface area at least 70 percent of the total surface area of the device. In the first device described above, i.e., the device consisting essentially of an elastomer, all surfaces of the devices will be elastomer surfaces. In the second device described above, i.e., the laminate device, part of the surface of the device need not be an elastomer surface, although in the preferred laminates, the said two substantailly parallel relatively large surface areas will both be elastomer surfaces in this type of device. It is also specified in the above descriptions of the novel vaginal devices of this invention that both of the relatively large parallel surfaces be able to contact vaginal epithelial tissue when, of course, the device has been inserted into a human vagina.

In order to visualize the meaning of these descriptive and limiting phrases, it will be useful to consider one embodiment of these devices, namely a device in the shape of a flat relatively thin rectangular sheet of uniform thickness. The total surface area of such a sheet will be the sum of relatively large top and bottom areas plus the areas of each of the four edges. And the sheet must be thin enough so that the sum of the relatively large top and bottom areas is of at least 70 percent of the total surface area of the sheet. The novel devices can, of course, be other than rectangular and other than flat.

The relatively large elastomer surface are described as being substantially parallel. This means that the device is of uniform thickness. A more precise meaning, and the meaning which is intended, is that in all of the novel vaginal devices of this invention, all normals constructed at any point on one relatively large surface and extended to the other relatively large surface are to be of substantially equal length. For ease of production, it is preferred that the substantially parallel relatively large elastomer surfaces of these novel vaginal devices be substantially planar, thus describing substantially flat devices. However, the novel devices of this invention include devices wherein the substantially parallel relatively large elastomer surfaces are other than planar. For example, these large surfaces may be wavy, ridged, dimpled, or corrugated as long as the two surfaces are substantially parallel as above defined. Thus a convex dimple or protrusion of any shape on one large surface must be compensated for by a corresponding concave dimple or intrusion of the same shape on the other large surface so that the two large surfaces are substantially parallel at all points on the surfaces. This limitation does not, however, exclude a few hook-like or barb-like elastomeric projections on either or both sides of a device to aid in retention of the device of the vagina. As an alternative to such elastomeric projections, other projection material is used, for example stainless steel, the projection being embedded in elastomer surfaces by methods known in the art.

It is specified above that both of the substantially parallel relatively large elastomer surfaces of these novel vaginal devices to able to contact vaginal epithelial tissues. This limitation excludes devices in the shapes of hollow spheres, hollow cylinders, deep cups, and the like which are not contemplated as being within scope of this invention. But the novel vaginal devices can be of any other shape, for example, shallow bowl shape, shallow plate shape, shallow cup shape, as long as all portions of both relatively large parallel surfaces are such that they could contact some portion of the epithelial tissues of a normal healthy vagina of a woman mature enough to be capable of ovulation. It is not necessary, however, that all portions of the large surfaces actually be in contact with vaginal epithelial tissue when the device is in a human vagina.

It is possible, of course, to distort any of these flexible resilient vaginal devices, for example by rolling or folding, so that a surface of the device so distorted could not contact vaginal epithelial tissue. The novel vaginal devices of this invention are defined herein in a relaxed state and such possible distored shapes are not relevant in a defining these novel devices.

When a device is in a human vagina, it may flex to a moderate extent, since it is flexible, in adapting to the inner contours of the vaginal cavity. However, it is specified in the above descriptions of the novel vaginal devices of this invention that the combustion of the resiliency of the polysiloxane elastomer and the distance between the substantially parallel relatively large elastomer surfaces, i.e., the thickness of the device, be such that both of these surfaces remain either in contact with vaginal epithelial tissues or exposed to the fluids in the vaginal cavity when the device is actually in the vaginal cavity. In other words, if the device is unduly thin or not sufficiently resilient, it will tend to fold, roll, or curl inside of the vagina so that parts of one or both of the relatively large surfaces of the device will not be exposed to vaginal fluids. This will result in an undesirably irregular prostaglandin release rate. Such devices are not within the scope of this invention.

Such factors as abortifacient or oxytocic potency of a prostaglandin and its lipophilicity might result in the dimensions of a device otherwise in accord with the first type of those defined above, i.e., the device consisting essentially of a flexible resilient non-toxic polysiloxane elastomer, being such that the device would fold, roll, or curl to an unacceptable degree in the vagina. In such situations, the second type of device described above, i.e., the laminate device, is especially appropriate. These devices are generally sandwich-like in nature. One layer of the laminate is a flexible resilient non-toxic polymeric solid substantially free of prostaglandin. The shape of this solid layer is substantially the same as that of the final device, i.e., having two substantially parallel relatively large surfaces with combined surface area at least 70 percent of the total surface area of solid layer. But the total linear dimensions of this solid layer will be somewhat less than the total linear dimensions of the final device since one or both of the relatively large surfaces of this solid layer are to be totally covered by a coextensive layer of the same flexible resilient non-toxic polysiloxane elastomer impregnated with abortifacient or oxytocic prostaglandin used in the first of the above-described novel vaginal devices, and the other surfaces of the solid layer are to be optionally covered with the same prostaglandin-impregnated polysiloxane elastomer or left uncovered. The purpose of this solid layer free of prostaglandin is to add sufficient rigidity to the final device to make possible the use of sheets of polysiloxane elastomer impregnated with prostaglandin which by themselves would fold, roll, or curl to an unacceptable degree in the vagina.

The flexible resilient polymeric solid substantially free of prostaglandin to be used in this laminate version of the novel vaginal devices of this invention can be any polymeric solid medically acceptable for vaginal use, including the same polysiloxane elastomer used in the prostaglandin-containing portions of this laminate device. See also U.S. Pat. Nos. 3,545,439 and 3,920,805 for other acceptable polymeric solids. Still another and preferred polymeric solid is a water-permeable water-insoluble gelatin sponge of the type described in U.S. Pat. No. 2,465,357, sold under the name Gelfoam®. The polymeric solid used, however, should be of flexibility and resiliency suitable to give the proper resiliency to the total device as defined hereinabove.

For ease of manufacture, it is preferred that only one or both of the relatively large parallel surfaces of polymeric solid layer of the laminate be covered with prostaglandin-containing polysiloxane polymer layers, the other, usually edge, areas of the polymeric solid being left uncovered. In manufacture of these laminate devices, the prostaglandin-containing polysiloxane elastomer portions are advantageously prepared first as described above for the first type of novel vaginal device of this invention. Then these usually sheet-like elastomer portions are bonded to the polymeric solid portion of the device with any medically acceptable adhesive which is also, of course, compatible with the polysiloxane elastomer and the polymeric solid portion. An especially suitable adhesive for this purpose is a thin layer of the same liquid polysiloxane prepolymer used to make the prostaglandin-containing polysiloxane elastomer portion of the final vaginal device. If an RTV type of prepolymer is used, catalyst is also added to the prepolymer at the appropriate time. The bonding prostaglandin-containing polysiloxane elastomer and polymeric solid, for example the gelatin sponge, with this adhesive is then accomplished by vulcanization of the thin prepolymer adhesive layer in the same manner used to vulcanize the prostaglandin-containing polysiloxane elastomer portion itself.

It is specified in the above descriptions of the novel vaginal devices of this invention that the amount of abortifacient or oxytocic prostaglandin be at least an effective amount of accomplish the desired abortion or induction of labor. Vaginal devices containing no more than the minimum amount of prostaglandin are operable although the rate of release of the prostaglandin from the device will decrease as exhaustion of the prostaglandin approaches. Therefore, it is preferred that more prostaglandin than this minimal effective amount be used to maintain a favorable concentration gradient throughout the polysiloxane elastomer matrix portions of the vaginal devices. However, one of the principal advantages of the novel vaginal devices of this invention over prior art vaginal devices, for example, the vaginal rings of U.S. Pat. No. 3,545,439, is that large excesses of drug to be released, here prostaglandin, are not necessary. Thus the total amount of prostaglandin in one of the novel vaginal devices of this invention is acceptably in the range about 2 to about 10 times the minimum amount effective to accomplish the desired abortion or induction of labor. A total amount of prostaglandin in the range about 1.5 to about 4 times the minimum effective amount is actually preferred when, as is preferred, the two substantially parallel relatively large elastomer surfaces of the first type of device and of the preferred form of the second or laminate type of device have a combined surface area at least 85 percent of the total surface area of the device.

It is further specified in the above descriptions of the novel vaginal devices of this invention that the polysiloxane elastomer of the first type of device and the polysiloxane elastomer portions of the second or laminate type of device be substantially uniformly impregnated with the abortifacient or oxytocic prostaglandin except at the elastomer surfaces, and that there be substantially no prostaglandin at any of the relatively large elastomer surfaces of either type of device.

It has been observed that polysiloxane elastomer vaginal rings fabricated from an RTV-type of dimethylpolysiloxane prepolymer and impregnated with the prostaglandin (15S)-15-methyl-PGF$_{2\alpha}$ methyl ester, both according to U.S. Pat. No. 3,545,439 and Kirton et al., Contraception, 8, 561, (1973), gave initial high blood levels of this prostaglandin when administered intravaginally to pregnant rhesus monkeys. See Spilman et al., above cited. These initial blood levels, measured at one hour after ring insertion, decreased rapidly in subsequent hours after ring insertion.

These initial high blood levels of prostaglandin would be medically unacceptable for administration of the prostaglandins to humans. I have now found that these initial high bursts of prostaglandin are not released from vaginal devices according to this invention when there is no substantial amount of prostaglandin at any of the relatively large polysiloxane elastomer surfaces of my devices. Rather, relatively uniform blood levels of prostaglandin are attained and maintained with the novel vaginal devices of this invention.

One method of obtaining vaginal devices according to this invention with substantially no prostaglandin at the relatively large elastomer surface of the device is to incubate the entire device if its is of the first type described above or the polysiloxane elastomer portions of the laminate type of device, the second type described above, in water at about normal human body temperature (about 37° C.) until there is substantially no prostaglandin at these polysiloxane elastomer surfaces. An entire laminate device could also be so treated provided that the polymeric solid portion of the laminate whih contains no prostaglandin can survive this treatment. When, as is preferred, this polymeric solid is gelatin sponge, the sponge may be somewhat softened and swollen by this treatment, an event which is not disadvantageous when it occurs in the vagina, but which should preferably not happen before insertion of the device into the vagina. The time necessary for this aqueous treatment to remove prostaglandin at the elastomer surface will vary with the particular prostaglandin. For devices containing (15S)-15-methyl-PGF$_{2\alpha}$ methyl ester, a one-hour incubation is usually sufficient to give a vaginal device that does not release an undesirable burst of prostaglandin when inserted into the human vagina.

This water incubation technique for preparing vaginal devices of this invention is not pharmaceutically elegant. But there is an alternative technique. I have made the surprising and unexpected discovery that polysiloxane elastomer devices of the first type described above and the polysiloxane elastomer portions of the laminate type of device described above can be made by a direct vulcanization and molding technique such that prostaglandin is substantially uniformly distributed throughout the elastomer except that there is substantially no prostaglandin at the relatively large parallel elastomer surface. The procedure for doing this will now be described.

As mentioned above and as will be exemplified below, the polysiloxane elastomer impregnated with prostaglandin used in the novel vaginal devices of this invention is prepared by vulcanization of a uniform suspension of the prostaglandin in the corresponding liquid polysiloxane prepolymer. Typically, this vulcanization is carried out in rigid-wall molds which will either give the final shape to the device or to the polysiloxane elastomer portion in the case of the laminate type of device, or preferably will provide a larger piece of prostaglandin-impregnated polysiloxane elastomer from which the final vaginal devices can be cut or punched. In this second procedure, advantageously the relatively large substantially parallel surface of the final device or the polysiloxane elastomer portions of the laminate type of device are created in this vulcanization-molding process and the distance between said relatively large surfaces (thickness) of the polysiloxane elastomer is thus fixed. The other dimensions and shape of the final vaginal device are determined by how large and what shape a piece is taken, cut, or punched from the larger molded elastomer sheet.

I have found that vulcanization of the mixture of liquid polysiloxane prepolymer, silica filler, and prostaglandin between rigid plates coated with polytetrafluoroethylene (Teflon®) with the plates held in contact with said mixture under moderate pressure results in relatively large parallel polysiloxane elastomer surfaces with substantially no prostaglandin at said surfaces. Vaginal devices made from such elastomers with (15S)-15-methyl-PGF$_{2\alpha}$ methyl ester or the prostaglandin and otherwise in accord with this invention when inserted into the vaginal cavities of pregnant rhesus monkeys give prostaglandin blood levels with either no or substantially smaller initial blood level peaks (burst) than those observed by Spilman et al., above cited, with the use of vaginal rings containing the same prostaglandin and using the same polysiloxane prepolymer.

Rigid mold plates coated with polytetrafluoroethylene (Teflon®) suitable to attain this result are exemplified below. However other plates which provide a relatively smooth relatively non-porous homogenous coating of polytetrafluoroethylene made by coating techniques known in the art will give the same result. See, for example, the discussion of polytetrafluoroethylene and technology for its use in Kirk-Othmer, "Encyclopedia of Chemical Technology," Interscience Publishers, New York, N.Y., 2d. Ed. Volume 9, pp. 805-831 (1966), and references cited therein. Of the various forms of polytetrafluoroethylene available, including granular polymers, coagulated dispersion polymers, and liquid dispersions, the latter two are most suitable for perparing coated mold plates for use in accord with this invention, especially the polytetrafluoroethylene liquid dispersion forms. Relatively smooth rigid metal plates for example aluminum or stainless steel, with the surface conformation desired in the final relatively large parallel polysiloxane elastomer surfaces of the vaginal devices of this invention are especially suitable for coating with the polytetrafluorethylene. A coating thickness for the polytetrafluoroethylene in the range about 1 to about 5 mil is usually satisfactory for these plates.

It is also specified above in the descriptions of the novel vaginal devices of this invention that the combination of the total elastomer surfaces of a vaginal device and the concentration of prostaglandin in the device be suitable for a medically acceptable release rate of the prostaglandin to accomplish an abortion or to induce labor according to those aspects of this invention. What is a medically acceptable release rate of any particular abortifacient or oxytocic prostaglandin will depend on such factors as the abortifacient or oxytocic potency of the prostaglandin and its half life in contact with vaginal epithelial tissue or in the blood streams and other body means which carry the prostaglandin to the target organ, the uterus, and any undesirable side effects which the prostaglandin may cause, for example, nausea, vomiting, and diarrhea. It is within the skill of the art, however to use pregnant rhesus monkeys and other subhuman primates to approximate suitable blood levels of each prostaglandin to be used subsequently with reasonable safety in humans to accomplish abortions and induction of labor in accord with this invention.

Next, it must be determined whether a particular vaginal device within the scope of this invention and containing that particular prostaglandin will provide that desired release rate. This is also within the skill of the art and will be examplified below with (15S)-15-methyl-PGF$_{2\alpha}$ methyl ester. Release rates are first determined in vitro according to procedures used for other drugs. See, for example, Roseman, J. Pharm. Sci. 61, 46 (1972). When suitable prostaglandin concentrations and vaginal device dimensions and geometry are approximated in accord with the in vitro study results, in vivo studies in pregnant rhesus monkeys are then used to determine the various parameters for a vaginal device or series of devices which would be safe to test in pregnant women.

My invention can be better understood from the examples which follow. In the vaginal devices which are described, the polysiloxane elastomer portion are prepared by vulcanization of a liquid dimethylpolysiloxane prepolymer containing finely divided silica and sold by Dow Corning Corporation, Midland, Mich. as Silastic 382 medical grade elastomer base; specific gravity 1.10 to 1.16; viscosity 35,000 to 70,000 centipoises; color light to medium gray. This material is agitated before use to assure that the silica filler is uniformly distributed througout the material.

EXAMPLE 1

Vaginal Device

Finely divided crystalline (15S)-15-methyl-$PGF_{2\alpha}$ methyl ester (8.473 g.) is triturated with a small amount of Silastic® 382. Additional Silastic® 382 (total 1686.22 g.) is added to this with thorough mixing in a Ross dough mixer. Portions of this mix (99.745 g. each) are each mixed thoroughly with stannous 2-ethylhexanoate (0.255 g.). Each such portion is placed on a square ⅜ in. flat aluminum plate 12 in. on each side and coated with Teflon® to a 1.5-mil thickness. A spacer of total thickness 0.20 cm. is placed at each corner of the plate, and a similar Teflon® coated plate is placed on top of the first plate, contact of the mix with both plates being at the Teflon® surface of each plate. The plates are fastened together with nuts and threaded bolts, the nuts being tightened to 150 in.-lbs. with a torque wrench. The plate-mix combination is placed in an oven at about 40° C. for 2 hours. Then the cured prostaglandin-impregnated sheet is removed from the plates and vaginal devices are cut with a 4.70 × 2.73 cm. elliptical punch. Average weight of device 2.195 g. Average thickness of device 0.192 cm. The devices are sterilized with ethylene oxide for 16 hours at 7½ psi at zero humidity, and are then degassed for 16 hours before packaging. Each device contains 0.5 weight percent of (15S)-15-methyl-$PGF_{2\alpha}$ methyl ester with a total of about 11 mg. of prostaglandin per device. The combined surface area of the two relatively large parallel surfaces of each device is 20 cm.².

Following the procedure of Example 1 but using twice as much of the same prostaglandin with the same amount of Silastic® and spacers of total thickness 0.1 cm, at each plate corner, elliptical devices are obtained which contain 1.0 weight percent of (15S)-15-methyl-$PGF_{2\alpha}$ methyl ester with a total of about 11 mg. of prostaglandin per device, a thickness of 0.1 cm., and 20 cm.². combined surface area of the two relatively large parallel surfaces.

Also following the procedure of Example 1, other vaginal devices are made wherein the combined surface area of the two parallel large surfaces is in the range 10 to 50 cm.², wherein the concentration range is 0.1 to 3 percent, and wherein the distance between the parallel relatively large elastomer surface is in the range 0.05 to 0.5. Among these additional vaginal devices, prostaglandin concentration ranges of 0.2 to 1.5 percent are preferred.

EXAMPLE 2

Vaginal Laminate Device

Following the procedure of Example 1 but using a mixture of 27.59 g. of (15S)-15-methyl-$PGF_{2\alpha}$ methyl ester with 1219.0 g. of Silastic® 382, 24.9 g. of this mixture per mold plate mixed with 0.068 g. of stannous 2-ethylhexanoate, and a single 0.025-cm. spacer at each corner of the plate, thin sheets of polysiloxane elastomer impregnated with the prostaglandin are obtained. From each such sheet, rectangular sections are cut with an 8 × 12.5 cm. punch. A small amount of freshly catalyzed Silastic® 382 is spread thinly on a glass plate, and one of the prostaglandin-containing cut elastomer sheets is pressed into the thin layer on the glass plate. Then the thus coated elastomer sheet is placed evenly on one of the large surfaces of a 8 × 12.5 cm. rectangular sheet of compressed foamed gelatin about 0.3 cm. thick (Gelfoam®, size 100 of the Upjohn Company, Kalamazoo, Michigan). Then a second thus coated prostaglandin-impregnated elastomer sheet is placed evenly on the other side of the foamed gelatin sheet. A piece of smooth paper is placed on one large side of this laminate, and the laminate is compressed uniformly with a rubber brayer. Then, smooth paper is placed on both large sides of the laminate, and the whole is placed between smooth rigid sheets of a methyl methacrylate polymer (Plexiglas®). The whole is weighted with ¾-inch aluminum plates and placed in an oven at about 40° C. for 2 hours. From the resulting laminate sheet, vaginal devices are cut with a 4.70 × 2.73 cm. elliptical punch. These devices are sterilized with ethylene oxide and then degassed as in Example 1. Each device contains 1.5 weight percent of (15S)-15-methyl-$PGF_{2\alpha}$ methyl ester. The combined surface area of the two relatively large parallel surfaces of each device is 20 cm.².

EXAMPLE 3

Abortion Using Vaginal Devices.

Healthy pregnant women approved for abortion and within the 6th to 24th week of pregnancy are chosen. The woman is placed under bed rest, and a vaginal device containing either 0.5 weight percent of (15S)-15-methyl-$PGF_{2\alpha}$ methyl ester or 1.0 weight percent of this prostaglandin, both produced as described in Example 1, is inserted high into the posterior fornix of the vagina with a sponge forceps and left there for the times specified below.

In 77 women with mean gestational age 13.6 weeks, the 0.5 percent device caused successful abortions in 90.9 percent of the women, the abortions being completed in 77.9 percent and incomplete in the others. Incomplete abortions were completed by curettage or sponge treatment of the uterus. The means abortion time for this entire successful group was 17.0 hours. The device is removed after abortion or when there has been total failure to abort within 48 hours.

In 58 women with mean gestational age 15.0 weeks, the 1.0 percent device caused successful abortions in 94.8 percent of the women, the abortions being complete in 79.3 percent and incomplete in the others. Incomplete abortions were completed by curettage or sponge treatment of the uterus. The mean abortion time for this entire successful group was 16.1 hours. The device is removed after abortion or when there has been total failure to abort within 48 hours.

In both of these studies, the term complete abortion includes not only abortions wherein the embryonic and placental components of gestation have been expelled in their entirety, but also abortions wherein products of conception remain in the vagina or dilated external cervical os but are removable therefrom manually or by sponge or ovum forceps. The term incomplete abortion defines those abortions wherein products of conception remain in the uterus but which are removable therefrom by surgical techniques usually used in such situations.

In the women who were treated with the 0.5 percent device the side effect rates were lower than those encountered with other methods for administering prostaglandins for abortion, there being among the 77 women, 34 percent incidence of vomiting with a median number of 2 episodes, 40 percent incidence of diarrhea with a median number of 2 episodes, no patients with chills, 2.6 percent incidence of flushing, and a mean blood loss of 140 ml. Among the 58 women treated with the 1.0 percent device, there was 55 percent incidence of vomiting with a median number of 2 episodes, 52 percent incidence of diarrhea with a median number of 3 episodes, 12.1 percent incidence of chills, 1.7 percent incidence of flushing, and a mean blood loss of 156 ml.

Peripheral plasma levels of (15S)-15-methyl-$PGF_{2\alpha}$ methyl ester in some of the women included in the above study were determined at various time intervals by radioimmunoassay procedures similar to those known in the art. When the 0.5 percent device was used, plasma levels of prostaglandin rose during the first hour to about 700 picograms per ml. and remained relatively stable until the device was removed. When the 1.0 percent device was used, plasma levels of prostaglandin rose during the first hour to about 2400 picograms and then fell between one and four hours to about the level observed with use of the 0.5 percent device. Although these results indicate some burst effect for the 1.0 percent device, the degree of burst is substantially less than would have been expected had there been a substantial amount of prostaglandin at the surfaces of the devices.

Some of the vaginal devices which caused successful abortions were analyzed for residual prostaglandin after use. The average amount of prostaglandin lost was about 2 mg.

EXAMPLE 4

Use of Vaginal Devices in Monkeys.

The methods and procedures for testing vaginal devices containing (15S)-15-methyl-$PGF_{2\alpha}$ methyl ester are described in Spilman et al., above cited, the radioimmunoassay procedure mentioned therein for analaysis of (15S)-15-methyl-$PGF_{2\alpha}$ methyl ester being similar to those known in the art. In place of the vaginal rings used by Spilman et al., vaginal devices according to this invention are used. Devices somewhat smaller than those used for humans are sometimes appropriate for these monkey studies because of differences between human and monkey vaginal cavities. Plasma levels of (15S)-15-methyl-$PGF_{2\alpha}$ methyl ester are determined at hourly or at shorter or longer time intervals after insertion of the device into the monkey vagina as described for ring insertion in Spilman et al.

Following the procedure of Examples 4, in vivo release rates of abortifacient and oxytocic prostaglandins from various polysiloxane elastomers are measured.

EXAMPLE 5

In Vitro Release Rates

Polysiloxane elastomer devices containing prostaglandin and intended for in vitro release rate studies are prepared and tested as follows:

The mold for the devices comprises a shallow circular perpendicular-wall cavity in a flat surface of a block of stainless steel. Advantageously the dimensions of the mold are such as to provide a circular surface area of 10 $cm.^2$ with a depth of about 0.3 cm. Also advantageously the block surface-well edge of the cavity is undercut slightly at a 45° angle. Polysiloxane prepolymer, silica filler when desired, prostaglandin, and catalyst are mixed as described in Examples 1 and 2, and the mix is placed in the cavity of the mold. A smooth flat Plexiglas plate is placed on the mix so as to cover it and the mold block surface, eliminating air bubbles on the surface of the mix and causing the mix surface to be flush with the mold block surface.

The mix is maintained at about 25° C. until vulcanization of the polysiloxane is complete. Then the resulting matrix is deflashed, and the entire mold block with prostaglandin-containing polysiloxane elastomer still in place is suspended in a covered jacketed 150-ml. beaker containing sufficient aqueous 0.1 molar THAM buffer at pH 7.0 (THAM is tris(hydroxyethyl)aminomethane) to cover the entire mold block including the polysiloxane surface. The solution is maintained at 37° C. with stirring. At various time intervals, samples (15-25 ml.) are taken, the volume lost being replaced with an equal volume of additional buffer solution.

The samples are extracted with chloroform to remove the prostaglandin from the buffer. When a prostaglandin ester is present, substantially all of the ester is extracted by the chloroform. When a prostaglandin free acid is present, the pH of the sample is lowered to about three with 0.2 molar pH 3 citrate buffer before chloroform extraction. The chloroform extracts are evaporated to dryness under redued pressure. The amount of prostaglandin in a withdrawn sample is then determined by analysis of the corresponding dry residue by methods known in the art.

Gas-liquid of chromatographic analytical procedures are especially useful for analysis of these residues. In the case of (15S)-15-methyl-$PGF_{2\alpha}$ methyl ester, a residue is silylated by treatment with 3-4 drops of dry pyridine and 0.5 ml. of bis(trimethylsilyl)trifluoroacetamide containing a small amount of cholesteryl acetate as an internal standard. This reaction mixture is maintained at about 25° C. for about 15 hours. Reference standards are prepared by silylation of the pure prostaglandin in the same manner.

For analysis, it is convenient to use a gas-liquid chromotographic apparatus with a glass column ¼-inch ID and a 4-foot length packed with 3% UCW-98 on gas Chrom Q, 80/100 mesh (sold by Applied Science Laboratories, State College, Pa.), 260° C. as column temperature, 270° C. as detector temperatures, gas flow with helium — 60 ml./min., air and hydrogen adjusted to maximize response, attenuation: 10 × 32 (Hewlett Packard Model 402, Skokie, Ill.). Unknown concentrations of the prostaglandin are calculated by comparison of peak areas with the reference standard which is injected with the sample.

Using the above procedure with the quantitative analysis part altered as needed in accord with the specific prostaglandin involved, in vitro release rates of abortifacient and oxytocic prostaglandins from various polysiloxane elastomers are measured.

Following the procedures of Examples 1, 2, 4, and 5, vaginal devices containing abortifacient or oxytocic prostaglandins in various polysiloxane elastomers are prepared. As mentioned above, the precise prostaglandin concentration in the device and the final geometry and dimensions of a device will be readily determined by those skilled in the art knowing what blood levels of a particular prostaglandin are needed in a human to accomplish the desired abortion or induction of labor, and measuring in vitro release rates, measuring in vivo release rates in monkeys, and finally, as in Example 3, measuring in vivo release rates in humans.

The novel vaginal devices of this invention are to be maintained at storage temperatures appropriate to the stability of the prostaglandin it contains. Moreover, although when prepared by the procedures described herein, the novel vaginal devices of this invention do not contain substantial amounts of prostaglandin at the relatively large elastomer surfaces of the devices, prolonged storage of the devices is likely to result in gradual diffusion of the prostaglandin to an elastomer surface and even accumulation of prostaglandin there. How fast this occurs will depend on the particular prostaglandin, the polysiloxane elastomer used, and the geometry and dimensions of the device. Vaginal devices containing (15S)-15-methyl-$PGF_{2\alpha}$ methyl ester and prepared according to Examples 1 and 2 are quite acceptable with regard to release rates in humans as in Example 3 after six months storage at about 4° C.

The procedure for radioimmunoassay of (15S)-15-methyl-$PGF_{2\alpha}$ methyl ester used herein is similar to the radioimmunoassay procedures known in the art for measuring small amounts of other abortifacient or oxytocic prostaglandins, and is within the skill of this art. See, for example, Salmon et al., Prostaglandins 10, 865 (1975).

I claim:

1. A vaginal device adapted for insertion and placement in the female human vaginal cavity and subsequent removal therefrom, for the administration of an abortifacient or oxytocic prostaglandin to the epithelial tissues of said cavity, said device consisting essentially of a flexible resilient non-toxic polysiloxane elastomer substantially uniformly impregnated except at the elastomer surface with at least an effective amount of said absortifacient prostaglandin to accomplish an abortion in a human during the first or second trimester or pregnancy or with at least an effective amount of said oxytocic prostaglandin to accomplish the induction of labor in a pregnant human at or near term, said prostaglandin being present in free acid form or in a more lipophilic ester form, said device having two substantially parallel relatively large elastomer surfaces with combined surface area at least 70 percent of the total elastomer surface area of the device, both of said parallel elastomer surfaces providing means for assuming a contour to be in substantial contact with the vaginal epithelial tissue, there being substantially no prostaglandin at said parallel elastomer surfaces of said device prior to vaginal insertion, the combination of the total elastomer surface area of said device and the concentration of prostaglandin in said device constituting a means for providing a medically acceptable release rate of said prostaglandin in the human vagina to accomplish said abortion of said induction of labor, and the combination of the resilience of said elastomer and the distance between said parallel elastomer surfaces being such that both of said parallel elastomer surfaces remain either in contact with said epithelial tissues or exposed to the fluids in said vaginal cavity when said device is in the vaginal cavity.

2. A device according to claim 1 wherein said prostaglandin is an abortifacient prostaglandin.

3. A device according to claim 2 wherein the two sustantially parallel relatively large elastomer surfaces have a combined surface area at least 85 percent of the total elastomer surface area of the device.

4. A device according to claim 3 wherein the parallel large elastomer surfaces are substantially planar.

5. A device according to claim 4 wherein the polysiloxane elastomer is a dimethylpolysiloxane.

6. A device according to claim 5 wherein the dimethylpolysiloxane elastomer is the type which is prepared by catalytic polymerization of the liquid dimethylpolysiloxane prepolymer in the range about 20°-40° C.

7. A device according to claim 6 wherein the abortifacient prostaglandin is of the $PGF_{\alpha}$-type and is present in the device in an amount about 2 to about 10 times the amount effective to accomplish an abortion in a human during the first or second trimester of pregnancy.

8. A device according to claim 7 wherein said prostaglandin is a methyl or ethyl ester.

9. A device according to claim 8 wherein said prostaglandin is (15S)-15-methyl-$PGF_{2\alpha}$ methyl ester.

10. A device according to claim 9 wherein the combined surface area of the two parallel large surfaces is in the range 10–50 square centimeters.

11. A device according to claim 9 wherein the prostaglandin is present in a concentration range 0.1–3%.

12. A device according to claim 9 wherein the prostaglandin is present in a concentration range 0.2–1.5%.

13. A device according to claim 9 wherein the distance between the parallel relatively large elastomer surfaces is in the range 0.05 to 0.5 centimeters.

14. A vaginal device adapted for insertion and placement in the female human vaginal cavity and subsequent removal therefrom, for the administration of an abortifacient or oxytocic prostaglandin to the epithelial tissues of said cavity, said device consisting essentially of a laminate having two substantially parallel relatively large surfaces with combined surface area at least 70 percent of the total surface area of the device, both of said parallel elastomer surfaces providing means for assuming a contour to be in substantial contact with the vaginal epithelial tissue, said device having a layer consisting essentially of a flexible resilient non-toxic polymeric solid substantially free of prostaglandin, with a shape and surfaces substantially the same as said device but with total linear dimensions smaller than those of said devices, said solid bonded on one or both of its relatively large parallel surfaces or on all of its surfaces to a coextensive layer of a flexible resilient non-toxic polysiloxane elastomer substantially uniformly impregnated except at the outer elastomer surface with a total of at least an effective amount of said abortifacient prostaglandin to accomplish an abortion in a human during the first or second trimester of pregnancy or of at least an effective amount of said oxytocic prostaglandin to accomplish the induction of labor in a pregnant human at or near term, said prostaglandin being present in free acid form or in a more lipophilic ester form, there being substantially no prostaglandin at the outer elastomer surfaces prior to vaginal insertion, the combination of the total outer elastomer surface area of said device and the total concentration of prostaglandin in said elastomer constituting a means for providing medically acceptable release rate of said prostaglandin in the human vagina to accomplish said abortion or said induction of labor, the resilience of said device being such that the elastomer on one or both of said parallel surfaces of said device is either in contact with said epithelial tissues or exposed to the fluids in said vaginal cavity when said device is in said vaginal cavity.

15. A device according to claim 14 wherein said prostaglandin is an abortifacient prostaglandin.

16. A device according to claim 15 wherein the flexible resilient non-toxic polymeric solid is the same polysiloxane elastomer to which said polymeric solid is bonded.

17. A device according to claim 15 wherein the flexible resilient non-toxic polymeric solid is a water-permeable water-insoluble gelatin sponge.

18. A device according to claim 17 wherein the gelatin sponge layer is bonded on both of its relatively large parallel surfaces to a coextensive layer of the prostaglandin-impregnated polysiloxane elastomer.

19. A device according to claim 18 wherein surfaces of the device other than the relatively large parallel surfaces are not bonded to the polysiloxane elastomer.

20. A device according to claim 19 wherein the two substantially parallel relatively large elastomer surfaces have a combined surface area at least 85 percent of the total surface area of the device.

21. A device according to claim 20 wherein the substantially parallel relatively large elastomer surfaces are substantially planar.

22. A device according to claim 21 wherein the polysiloxane elastomer is a dimethylpolysiloxane.

23. A device according to claim 22 wherein the dimethylpolysiloxane elastomer is the type which is prepared by catalytic polymerization of the liquid dimethylpolysiloxane prepolymer in the range about 20°–40° C.

24. A device according to claim 23 wherein the abortifacient prostaglandin is of the $PGF_\alpha$-type and is present in the device in an amount about 2 to about 10 times the amount effective to accomplish an abortion in a human during the first or second trimester of pregnancy.

25. A device according to claim 24 wherein said prostaglandin is a methyl or ethyl ester.

26. A device according to claim 25 wherein said prostaglandin is (15S)-15-methyl-$PGF_{2\alpha}$ methyl ester.

27. A device according to claim 26 wherein the combined surface area of the two parallel large surfaces is in the range 10–50 square centimeters.

28. A device according to claim 2 wherein said prostaglandin has a potency in the golden hamster pregnancy test at least equal to that of $PGE_2$.

29. A device according to claim 2 wherein said prostaglandin has a potency in the golden hamster pregnancy test at least 10 times that of $PGE_2$.

30. A device according to claim 2 wherein said prostaglandin has a potency in the golden hamster pregnancy test at least 100 times that of $PGE_2$.

31. A device according to claim 15 wherein said prostaglandin has a potency in the golden hamster pregnancy test at least equal to that of $PGE_2$.

32. A device according to claim 15 wherein said prostaglandin has a potency in the golden hamster pregnancy test at least 10 times that of $PGE_2$.

33. A device according to claim 15 wherein said prostaglandin has a potency in the golden hamster pregnancy test at least 100 times that of $PGE_2$.

34. A method of accomplishing an abortion in a female human during the first and second trimester of pregnancy which comprises inserting a device according to claim 2 into the vaginal cavity of said human.

35. A method of accomplishing an abortion in a female human during the first and second trimester of pregnancy which comprises inserting a device according to claim 9 into the vaginal cavity of said human.

36. A method of accomplishing an abortion in a female human during the first or second trimester of pregnancy which comprises inserting a device according to claim 15 into the vaginal cavity of said human.

37. A method of accomplishing an abortion in a female human during the first or second trimester of pregnancy which comprises inserting a device according to claim 26 into the vaginal cavity of said human.

38. A method of accomplishing an abortion in a female human during the first and second trimester of pregnancy which comprises inserting a device according to claim 28 into the vaginal cavity of said human.

39. A method of accomplishing an abortion in a female human during the first or second trimester of pregnancy which comprises inserting a device according to claim 29 into the vaginal cavity of said human.

40. A method of accomplishing an abortion in a female human during the first or second trimester of pregnancy which comprises inserting a device according to claim 30 into the vaginal cavity of said human.

41. A method of inducing menstruation in a sexually exposed female human capable of ovulation, which comprises inserting a device according to claim 2 into the vaginal cavity of said human at a time after the time of expected but missed menses.

42. A method according to claim 41 wherein said device is inserted at a time at least two weeks after the time of expected but missed menses.

43. A method of inducing menstruation in a sexually exposed female human capable of ovulation, which comprises inserting a device according to claim 9 into the vaginal cavity of said human at a time after the time of expected but missed menses.

44. A method according to claim 43 wherein said device is inserted at a time at least two weeks after the time of expected but missed menses.

45. A method of inducing menstruation in a sexually exposed female human capable of ovulation, which comprises inserting a device according to claim 15 into the vaginal cavity of said human at a time after the time of expected but missed menses.

46. A method according to claim 45 wherein said device is inserted at a time at least two weeks after the time of expected but missed menses.

47. A method of inducing menstruation in a sexually exposed female human capable of ovulation, which comprises inserting a device according to claim 26 into the vaginal cavity of said human at a time after the time of expected but missed menses.

48. A method according to claim 47 wherein said device is inserted at a time at least two weeks after the time of expected but missed menses.

49. A method of inducing menstruation in a sexually exposed female human capable of ovulation, which comprises inserting a device according to claim 28 into the vaginal cavity of said human at a time after the time of expected but missed menses.

50. A method according to claim 49 wherein said device is inserted at a time at least two weeks after the time of expected but missed menses.

51. A method of inducing menstruation in a sexually exposed female human capable of ovulation, which comprises inserting a device according to claim 29 into the vaginal cavity of said human at a time after the time of expected but missed menses.

52. A method according to claim 51 wherein said device is inserted at a time at least two weeks after the time of expected but missed menses.

53. A method of inducing menstruation in a sexually exposed female human capable of ovulation, which comprises inserting a device according to claim 30 into the vaginal cavity of said human at time after the time of expected but missed menses.

54. A method according to claim 53 wherein said device is inserted at a time at least two weeks after the time of expected but missed menses.

55. A method of inducing menstruation in a sexually exposed female human capable of ovulation, which comprises inserting a device according to claim 31 into the vaginal cavity of said human at a time after the time of expected but missed menses.

56. A method according to claim 55 wherein said device is inserted at a time at least two weeks after the time of expected but missed menses.

57. A method of inducing menstruation in a sexually exposed female human capable of ovulation, which comprises inserting a device according to claim 32 into the vaginal cavity of said human at a time after the time of expected but missed menses.

58. A method according to claim 57 wherein said device is inserted at a time at least two weeks after the time of expected but missed menses.

59. A method of inducing menstruation in a sexually exposed female human capable of ovulation, which comprises inserting a device according to claim 33 into the vaginal cavity of said human at a time after the time of expected but misses menses.

60. A method according to claim 59 wherein said device is inserted at a time at least two weeks after the time of expected but missed menses.

61. A method emptying the uterus of a human female when said uterus contains a dead fetus, a hydatidiform mole, or a combination of those, which comprises inserting a device according to claim 2 into the vaginal cavity of said human.

62. A method of emptying the uterus of a human female when said uterus contains a dead fetus, a hydatidiform mole, or a combination of those, which comprises inserting a device according to claim 9 into the vaginal cavity of said human.

63. A method of emptying the uterus of a human female when said uterus contains a dead fetus, a hydatidiform mole, or a combination of those, which comprises inserting a device according to claim 15 into the vaginal cavity of said human.

64. A method of emptying the uterus of a human female when said uterus contains a dead fetus, a hydatidiform mole, or a combination of those, which comprises inserting a device accoring to claim 26 into the vaginal cavity of said human.

65. A method of emptying the uterus of a human female when said uterus contains a dead fetus, a hydatidiform mole, or a combination of those, which comprises inserting a device according to claim 28 into the vaginal cavity of said human.

66. A method of emptying the uterus of a human female when said uterus contains a dead fetus, a hydatidiform mole, or a combination of those, which comprises inserting a device according to claim 29 into a vaginal cavity of said human.

67. A method of emptying the uterus of a human female when said uterus contains a dead fetus, a hydatidiform mole, or a combination of those, which comprises inserting a device according to claim 30 into the vaginal cavity of said human.

68. A method of emptying the uterus of a human female when said uterus contains a dead fetus, a hydatidiform mole, or a combination of those, which comprises inserting a device according to claim 31 into the vaginal cavity of said human.

69. A method of emptying the uterus of a human female when said uterus contains a dead fetus, a hydatidiform mole, or a combination of those, which comprises inserting a device according to claim 32 into the vaginal cavity of said human.

70. A method of emptying the uterus of a human female when said uterus contains a dead fetus, a hydatidiform mole, or a combination of those, which comprises inserting a device according to claim 33 into the vaginal cavity of said human.

71. A method of accomplishing an abortion in a female human during the first or second trimester of pregnancy which comprises inserting a device according to claim 31 into the vaginal cavity of said human.

72. A method of accomplishing an abortion in a female human during the first or second trimester of pregnancy which comprises inserting a device according to claim 32 into the vaginal cavity of said human.

73. A method of accomplishing an abortion in a female human during the first or second trimester of pregnancy which comprises inserting a device according to claim 33 into the vaginal cavity of said human.

* * * * *

UNITED STATES PATENT AND TRADEMARK OFFICE
CERTIFICATE OF CORRECTION

PATENT NO. : 4,043,339
DATED : August 23, 1977
INVENTOR(S) : Theodore J. Roseman It is certified that error appears in the above-identified patent and that said Letters Patent are hereby corrected as shown below:

Column 9, line 10 should read:--homogenous and substantially free of holes, pores, channels and the like which would allow water permeation --
Column 9, line 13: "vulcanizating" should read -- vulcanizing --.
Column 10, line 60: "combustion" should read -- combination --.
Column 15, line 3: "portion" should read -- portions --.
Column 16, line 47: "means" should read -- mean --.

Signed and Sealed this

Sixth Day of June 1978

[SEAL]

Attest:

RUTH C. MASON
Attesting Officer

DONALD W. BANNER
Commissioner of Patents and Trademarks